United States Patent
Rajaram et al.

(10) Patent No.: US 10,005,747 B2
(45) Date of Patent: Jun. 26, 2018

(54) PROCESS FOR THE PRODUCTION OF γ-VALEROLACTONE

(71) Applicant: Council of Scientific and Industrial Research, New Delhi (IN)

(72) Inventors: Bal Rajaram, Mohkampur (IN); Pendem Chandrashekar, Mohkampur (IN); Bordoloi Ankur, Mohkampur (IN); Konathala Laxmi Narayan Sivakumar, Mohkampur (IN); Manoj Kumar, Mohkampur (IN); Saran Sandeep, Mohkampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days. days.

(21) Appl. No.: 15/207,312

(22) Filed: Jul. 11, 2016

(65) Prior Publication Data

US 2017/0022175 A1    Jan. 26, 2017

(30) Foreign Application Priority Data

Jul. 24, 2015 (IN) .......................... 2252/DEL/2015

(51) Int. Cl.
| | |
|---|---|
| *C07D 307/33* | (2006.01) |
| *B01J 23/42* | (2006.01) |
| *B01J 27/236* | (2006.01) |
| *B01J 37/08* | (2006.01) |
| *B01J 37/18* | (2006.01) |
| *B01J 37/02* | (2006.01) |

(52) U.S. Cl.
CPC ............ *C07D 307/33* (2013.01); *B01J 23/42* (2013.01); *B01J 27/236* (2013.01); *B01J 37/0201* (2013.01); *B01J 37/08* (2013.01); *B01J 37/18* (2013.01)

(58) Field of Classification Search
CPC ....... C07D 307/33; B01J 23/42; B01J 27/236; B01J 37/08; B01J 37/18; B01J 37/0201
See application file for complete search history.

(56) References Cited

PUBLICATIONS

Kuwahara, RSC Adv., 2014, 4, 45848-45855.*
Abdelrahman, ACS Catalysis, 2014, 4, 1171-1181.*
Narayanan, Applied Catalysis a: General, 147, 1996, L253-L258.*
Pendem, Green Chem, 2012, 14, 3107-3113.*
Galletti, Anna Maria Raspolli, et al., "A sustainable process for the production of γ-valerolactone by hydrogenation of biomass-derived levulinic acid", Green Chem., 2012, 14, 688-694, (Dec. 13, 2011), 688-694.
Hengne, Amol M., et al., "Cu-ZrO2 nanocomposite catalyst for selective hydrogenation of levulinic acid and its ester to γ-valerolactone", Green Chem., 2012, 14, 1064-1072, (Jan. 12, 2012), 1064-1072.
Mai, Estevão, et al., "Molybdenum carbide nanoparticles within carbon nanotubes as superior catalysts for γ-valerolactone production via levulinic acid hydrogenation", Green Chem., 2014, 16, 4092-4097, (Jul. 8, 2014), 4092-4097.
Shimizu, Ken-Ichi, et al., "Hydrogenation of levulinic acid to γ-valerolactone by Ni and MoOx co-loaded carbon catalysts", Royal Society of Chemistry, DOI: 10.1039/c4gc00735b, (Jun. 5, 2014), 5 pgs.
Tukacs, Jozsef M., et al., "Efficient catalytic hydrogenation of levulinic acid: a key step in biomass conversion", Green Chem., 2012, 14, 2057-2065, (Apr. 30, 2012), 2057-2065.
Upare, Pravin P., et al., "Nickelpromoted copper-silica nanocomposite catalysts for hydrogenation of levulinic acid to lactones using formic acid as a hydrogen feeder", Applied Catalysis A: General 491 (2015) 127-135, (Dec. 9, 2014), 127-135.
Wang, Jie, et al., "Zirconium-Beta zeolite as a robust catalyst for the transformation of levulinic acid to γ-valerolactone via Meerwein-Ponndorf-Verley reduction", RSC Adv., 2014, 4, 13481-13489, (Feb. 26, 2014), 13481-13489.
Wu, Zhijie, et al., "Selective conversion of cellulose into bulk chemicals over Brønsted acid-promoted ruthenium catalyst: one-pot vs. sequential process", Green Chem., 2012, 14, 3336-3343, (Sep. 13, 2012), 3336-3343.
Yan, Kai, et al., "A noble-metal free Cu-catalyst derived from hydrotalcite for highly efficient hydrogenation of biomass-derived furfural and levulinic acid", RSC Advances, 2013, 3, 3853-3856, (Jan. 23, 2013), 3853-3856.
Yan, Kai, et al., "Selective hydrogenation of furfural and levulinic acid to biofuels on the ecofriendly Cu—Fe catalyst", Fuel 115 (2014) 101-108, (Jul. 8, 2013), 101-108.
Yuan, Jing, et al., "Copper-based catalysts for the efficient conversion of carbohydrate biomass into γ-valerolactone in the absence of externally added hydrogen", Energy Environ. Sci., 2013, 6, 3308-3313, (Aug. 20, 2013), 3308-3313.
Zhou, Huacong, et al., "Cobalt catalysts: very efficient for hydrogenation of biomass-derived ethyl levulinate to gammavalerolactone under mild conditions", Green Chem, DOI: 10.1039/c4gc00482e, (Jun. 5, 2014), 6 pgs.

* cited by examiner

*Primary Examiner* — D Margaret M Seaman
(74) *Attorney, Agent, or Firm* — Schwegman Lundberg & Woessner, P.A.

(57) ABSTRACT

The present invention provides a process for the hydrogenation of the levulinic acid to γ-valerolactone in a single step with a single Pt supported on hydrotalcite catalyst. The process provides conversion of γ-valerolactone over Pt supported hydrotalcite catalyst at room temperature (25° C.). The process provides a levulinic acid conversion of 34-100% with 20-50 bar hydrogen pressure to give γ-valerolactone selectivity up to 99%.

5 Claims, 4 Drawing Sheets

PROCESS FOR THE PRODUCTION OF γ-VALEROLACTONE

CLAIM FOR PRIORITY

This application claims the benefit of priority of Indian Patent Application No. 2252/DEL/2015, filed Jul. 24, 2015, which application is incorporated herein in its entirety.

FIELD OF THE INVENTION

The present invention related to an improved process for the production of γ-valerolactone (GVL) by hydrogenation of leuvlinic acid (LA). The process provides hydrogenation of leuvlinic acid at room temperature over Pt-Supported on hydrotalcite catalyst using $H_2$ pressure. The process provides Leuvlicnic acid (LA) conversion up to 34% to 100% and selectivity of γ-valerolactone up to 99%.

BACKGROUND OF THE INVENTION

One of the most important task for chemists is the development of new technology for producing energy and chemicals from sustainable resources. Plant derived biomass provides an ideal alternative to fossil resources, which is diminishing very rapidly and lots of efforts have been devoted to the conversion of bio mass to diverse molecules that can be used to produce energy feedstock chemicals and fine chemicals such as n-butanol, ethanol, sorbitol, hydroxymethylfurfural, methylfurfural, γ-valerolactone (GVL). The γ-valerolactone is considered an interesting green, bio-based platform chemical with high application potential. The development of environmentally benign, cost effective process for the synthesis of GVL has received extensive attention in recently years. Although there have been reports for the hydrogenation of leuvlunic acid using molecular hydrogen or formic acid over homogeneous or heterogeneous catalysts but most of the cases the reaction temperature is very high. The main advantage of our process is that reaction was carried out at room temperature to get very high yield.

Reference can be made to the article in Green Chem 14, 2012, 2057-2065 by J M Tukacs et al. where they used molecular hydrogen in the presence of $Ru(acac)_3$ as homogeneous catalyst at 100 bar hydrogen pressure and 140° C.

Reference can be made to the article in Fuel 115, 2014, 101-108 by Kai Yan et al. where they reported 98.7% conversion of levulinic acid with 90.1% selectivity for GVL over Cu—Fe catalyst using 70 bar of hydrogen at 200° C.

Reference can be made to the article in Rsc Adv. 3, 2013, 3858-3856 by Kai Yan et al. where they reported >99% conversion of levulinic acid with 90.7% selectivity for GVL over Cu—Cr catalyst using 60 bar of hydrogen also.

Reference can also be made to the article in Green chem. 2014, 16, 4092-4097 by Estevao F Mai et al. where >99% conversion of levulinic acid with 90% selectivity for GVL is reported over $Mo_2C/CNT$ catalyst using 30 bar of hydrogen at 200° C.

Reference can be made to the article in Green Chem. 14, 2014, 1064-1072 by C. V. Rode et. al where they reported 100% conversion of levulinic acid with 100% selectivity for GVL over $Cu—ZrO_2$ (1:1) catalyst using 34.5 bar of hydrogen at 200° C.

Reference can also be made to the article in Energy & Environ Sci. 6, 2013, 3308-3313 by Yong Cao et al. where they reported is that 100% conversion of levulinic acid with 100% selectivity for GVL over 20% $Cu—ZrO_2$ catalyst using 40 bar of hydrogen at 200° C.

Reference can also be made to the article in Green Chem. 2014, 16, 3899-3903 by Ken-ichi Shimizu et al. to get 100% conversion of levulinic acid with 97% selectivity for GVL over Ni—MoOx/C catalyst using 8 bar of hydrogen at 140° C. in 5 hours reaction time.

Reference can be made to the article in RSC Adv. 2014, 4, 13481-13489 by J Wang et al. where they used Zr-Beta Zeolite as a robust catalyst for liquid and gas phases hydrogenation of Levulinic acid with 96% selectivity in batch reactor around 99% selectivity of GVL was obtained in continuous flow reactor using hydrogen donor at ambient pressure and solvent boiling temperatures.

Reference can be made to the article in Green Chem. 2012, 14, 688-694 by A M R Galletti et al. where they reported the levulinic acid to GVL at 70° C. using 5 bar hydrogen pressure but in the presence of 5% Ru/C combination of acid co-catalyst like Amberlytst A70, Amberliyst A 15, niobium phosphate and niobium oxide. Levulicnic acid hydrogenation was also studied with the combination of Ru/C and Amberlyst A70 at 50° C. and conversion was reported as 85% and with 99.1% selectivity of GVL.

Reference can be made to the article in Applied Catal. A: General, 2015, 491, 127-135 by Praveen P Upare et al. where Nickel-promoted Copper-Silica nano composite catalyst was used for leuvlunic acid hydrogenation using formic acid as a hydrogen source. The catalyst selectively converts 99% of LA in to 96% GVL. The reaction was carried at 265° C. at 1 atm pressure in continues down flow reactor.

Reference can be made to the article in Green Chem., 2014, 163870-3875 by H Zhou et al. where they reported $Co_3O_4$ as the catalyst for the conversion of ethyl levulinate to γ-valerolactone at 130° C. and 33 bar $H_2$ bar hydrogen pressure.

Reference can be made to the article in Green Chemistry., 2012, 14, 3336-3343 by Zhijie Wu et al. where the combination of hydrolysis reaction and hydrogenation/hydrogenolysis of cellulose to GVL by MCM-41-1.5-$SO_3$—H and Ru/C is reported at 230° C. and 6 bar hydrogen pressure in sequential process and single pot process. In both cases selectivity of GVL was obtained around 95%. But MCM-41-n-$SO_3$ was deactivated after reaction.

In all the above cases the reaction temperature was very high. The advantage of our catalyst is to produce γ-valerolactone at room temperature.

OBJECTS OF THE INVENTION

The main object of the present invention is to provide a catalyst for the production of γ-valerolactone (GVL) by hydrogenation of leuvlinic acid (LA) with high selectivity.

Another object of the present invention is to provide a process to produce γ-valerolactone form leuvlinic acid at room temperature. Yet another object of the present invention is to provide a process which operates in the pressure range between 20-50 bar.

Yet another object of the present invention is to provide a process which produce γ-valerolactone in the reaction time range between 2-100 h

SUMMARY OF THE INVENTION

Accordingly the present invention provides an improved process for the production of γ-valerolactone by hydrogenation of levulinic acid in batch reactor at room temperature and 50 bar H$_2$ pressure, in the presence of Pt supported hydrotalcite catalyst, with a reaction time between after 2-100 h.

DETAILED DESCRIPTION OF THE INVENTION

Figure 1:
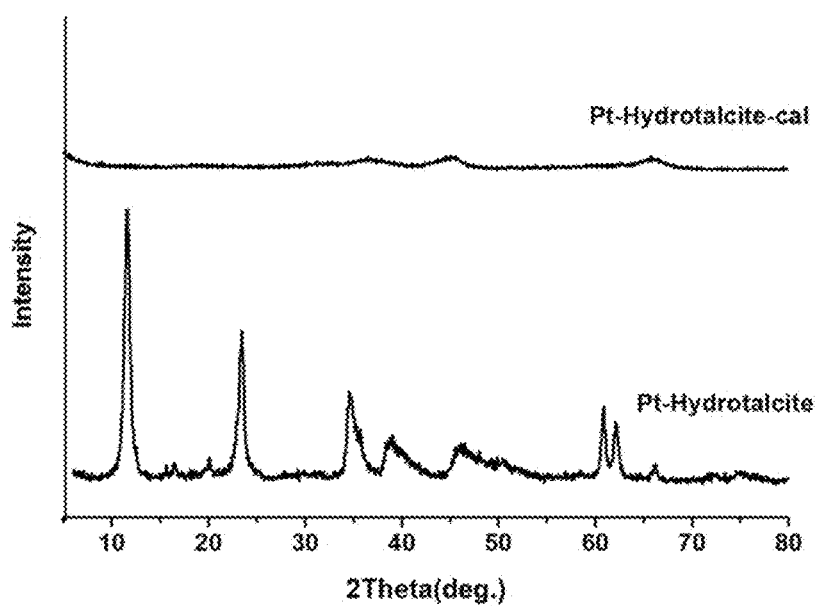
FIG. 1 X-ray Diffraction (XRD) of 2% Pt-hydrotalcite and calcined 2% Pt-hydrotalcite.

The present invention provides a process for the production of γ-valerolactone by hydrogenation at room temperature over Pt supported on hydrotalcite catalyst which involves the following steps.

The process for the preparation of hydrotalcite comprising the steps of:
Synthesis of hydrotalcite (Al$_2$O$_3$/MgO ratio of 80:20)
Synthesis of hydrotalcite was carried out using precipitation of Al (NO$_3$)$_3$. 9H$_2$O and
Mg(NO$_3$)$_2$6H$_2$O with NaOH and Na$_2$CO$_3$ solution.
The pH of the mixture was adjusted between 9-13.
The mixed solution was stirred for 30 min at room temperature.
Heating of the resultant solution was carried out in a two necked round bottom flask at 80-90° C. for 16-18 h to get a solid substance.
The solid obtained was filtered and washed with distilled water dried at 110° C. for 12 h.

In one embodiment of the present invention, an improved process for the production of γ-valerolactone comprising the steps: a) preparing hydrotalcite support using nitrate salts of aluminium and magnesium ratio of 80:20; b) impregnation of platinum in the range 1-3% on hydrotalcite using Pt (NH$_3$)$_4$(NO$_3$)$_2$ as Pt precursor; c) calcinating Pt loaded hydrotalcite as obtained from step (b) at 260-550° C. in air; d) reducing Pt loaded hydrotalcite as obtained from step (c) in hydrogen gas at 260-480° C. to obtain platinum supported hydrotalcite; e) hydrogenising of 5-20% leuvlinic acid in water in presence of platinum supported hydrotalcite catalyst as obtained in step (d) in high pressure stirrer reactor at 25° C. to 100° C. and 20-50 bar hydrogen gas while stirring for a period of 2-100 h to obtain γ-valerolactone In another embodiment of the present invention, A process accordingly to claim 1, wherein hydrogenising of leuvlinic acid (LA) is carried out at a temperature in the range between 75-100° C.

In yet another embodiment of the present invention, wherein hydrogenising of leuvlinic acid (LA) is carried out for time in the range 75-100 h.

In yet another embodiment of the present invention, wherein hydrogenising of leuvlinic acid (LA) is carried out at a pressure in the range of 40-50 bar hydrogen pressure.

In another embodiment of the present invention, wherein the levulinic acid concentration for its hydrogenation is preferably selected in the range 5-20%.

Loading of Pt on Hydrotalcite:
Pt was impregnated with the above prepared hydrotalcite using the following preparation method.
Pt(NH$_3$)$_4$(NO$_3$)$_2$ dissolved in required amount water and added to the hydrotalcite support while stirring and continued for 1 h. The Pt supported catalyst was dried at 90° C. for 12 and calcined at 550° C. The wt. % of Pt supported on HT varied in the range between 1-3.

General Procedure for the Hydrogenation of Levulinic Acid:

Hydrogenation reactions were conducted in batch mode, in a 160 ml stainless steel autoclave (parr reactor) at various temperatures. leuvlicnic acid, catalyst (reduced in H$_2$ at 480° C.) and water were placed inside the reactor, after which the reactor was closed. Then the system was purged with hydrogen 4 times to remove the air. The whole system was pressurized to require hydrogen pressure from 20 to 50 bars and carried hydrogenation reaction at room temperature 25° C. to 75° C. Aliquots (liquid) were withdrawn through the special sample port attached within the reactor. At the end of the reaction, the pressure was released very slowly. The catalyst particles were separated by filtration and the product was analyzed by an Agilent 7890 gas chromatograph equipped with a FID (using restek MXT WAX capillary Column 30 m×0.25ID) using reference samples.

The following examples are given by way of illustration of working of the invention in actual practice and should not be constructed to limit the scope of the present invention in any way.

Example: 1

Preparation of Pt Supported Hydrotalcite (HT) Catalyst

The hydroltalcite support was prepared by co-precipitation method. The procedure as follows. Salt solution A (100 ml) containing mixture of 0.080 mole Al(NO$_3$)$_3$.9H$_2$O and 0.020 mole Mg(NO$_3$)$_2$6H$_2$O was added drop wise to a basic solution of B (100 ml) containing 0.05 mole Na$_2$CO$_3$ and 0.17 mole NaOH. The pH was maintained between 9-13 and the mixture was aged for 1 h at room temperature with continuous stirring. Later temperature was raised to 80° C. and continued for 16 to 18 h. The resulted solid was washed with deionised water and dried at 110° C. in an oven for 12 h.

The Pt was deposited by wetness impregnation method. In a typical procedure, a 20 ml solution of 0.2 g of tetramine platinum nitrate nano hydrate (Pt(NH$_3$)$_4$(NO$_3$)$_2$) (2% on Pt basis) was mixed with 5 g of prepared hydrotalcite support stirred at room temperature for 1 h. The mixture was later dried at 60-80° C. at a duration of 2 to 4 h. The resulted solid was dried in an air oven at 110° C. for 12 h and calcined at 550° C. for 6 h.

Figure 2:
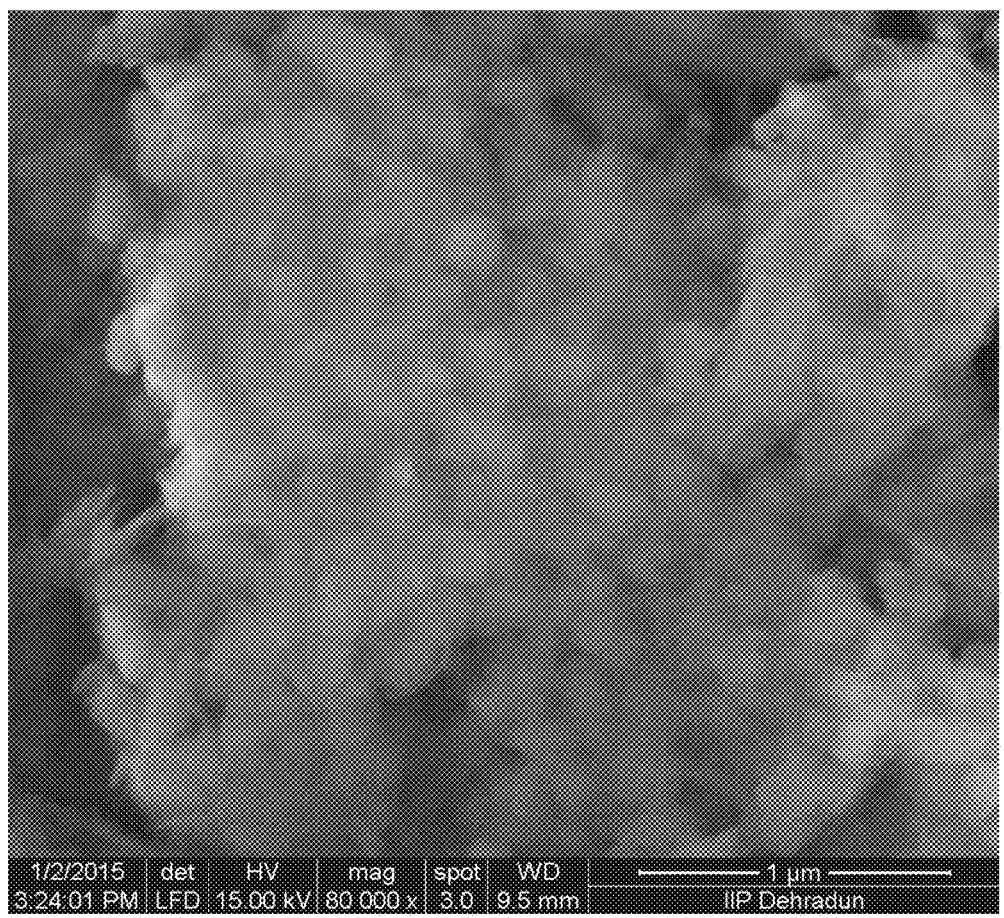
FIG. 2 Scanning Electron Microscope (SEM) image of 2% Pt-hydrotalcite
FIG. 3 EDAX of 2% Pt-hydrotalcite
FIG. 4 High magnification TEM image of 2% Pt-hydrotalcite
Figure 3:
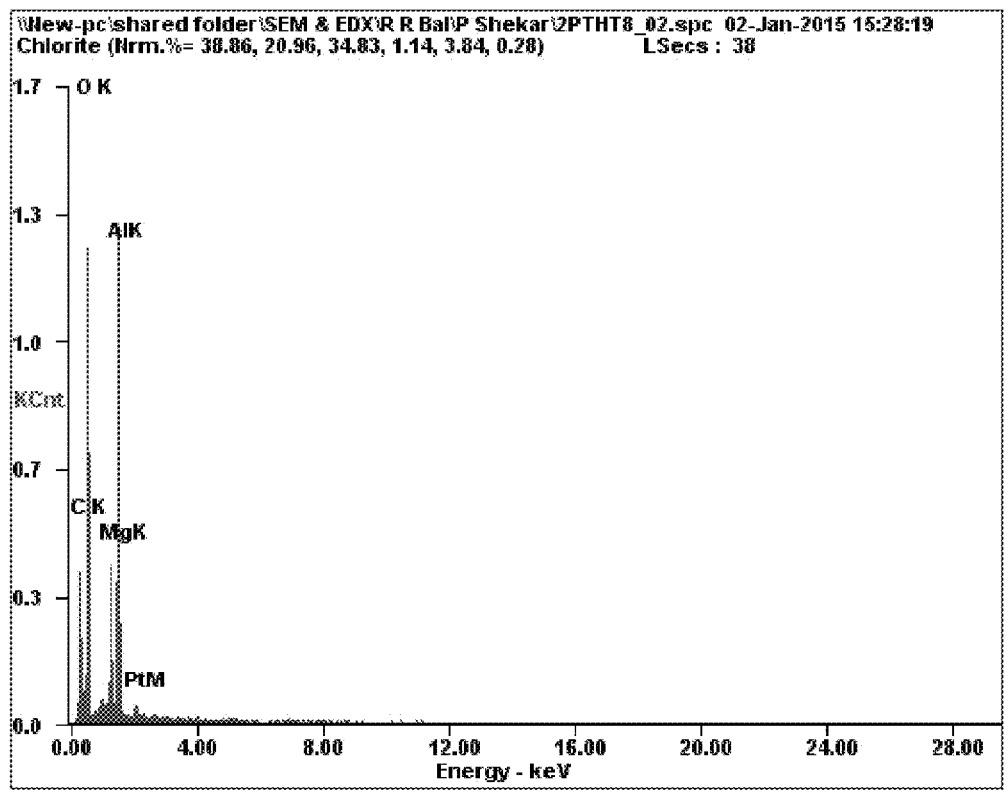
Figure 4:
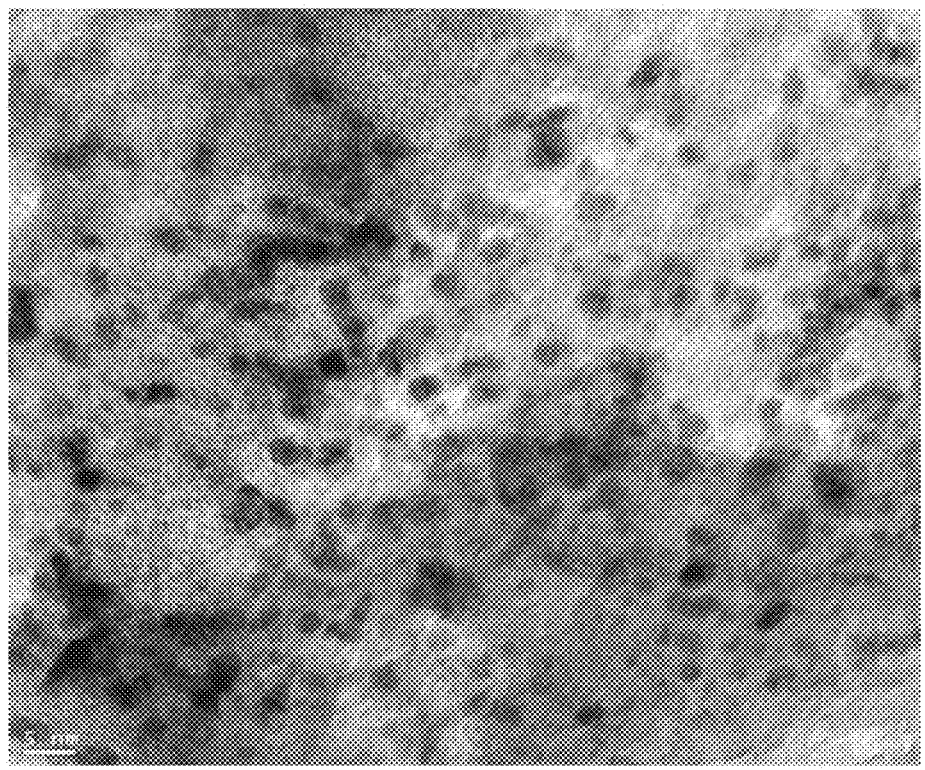

The obtained catalyst was denoted as 2% Pt-HT the catalyst. In the present case, the three different types of catalyst named 1% Pt-HT, 2% Pt-HT and 3% Pt-HT contains 1% (0.1 g), 2% (0.2 g), and 3% (0.3 g) of tetra mine platinum nitrate nano hydrate The XRD pattern of the hydrotalcite and 2% Pt hydrotalcite are shown in FIG. 1. XRD pattern of HT conforms the presence of LDH structure of hydrotalcite in the sample. 2% Pt-HT catalyst structure was collapsed after calcination of Pt-supported hydrotalcite catalyst was confirmed by XRD FIG. 1. Pt nanoparticle was not shown because of very small amount and small size. The morphology of the material (2% Pt-HT) was characterized by SEM. The typical image of the 2% Pt-HT is shown in FIG. 2. From the SEM image it is clear that the hydrotalcite particles are almost in uniform shape. The EDAX of 2% Pt-HT in FIG. 3 conforms the qualitative composition of Al, Mg, O, and Pt metals. The typical TEM images of the 2% Pt-HT is shown in FIG. 4, which indicate that 2-3 nm Pt nanoparticles are well dispersed on hydrotalcite support.

Example: 2

The hydroltalcite support was prepared by co-precipitation method. The procedure as follows: Salt solution A (100 ml) containing mixture of 0.080 mole $Al(NO_3)_3 \cdot 9H_2O$ and 0.020 mole $Mg(NO_3)_2 6H_2O$ was added drop wise to a basic solution of B (100 ml) containing 0.05 mole $Na_2CO_3$ and 0.17 mole NaOH. The pH was maintained between 9-13 and the mixture was aged for 1 h at room temperature with continuous stirring. Later temperature was raised to 80° C. and continued for 16 to 18 h. The resulted solid was washed with deionised water and dried at 110° C. in an oven for 12 h.

The Pt was deposited by wetness impregnation method. In a typical procedure a 20 ml solution of tetramine platinum nitrate nano hydrate (Pt $(NH_3)_4(NO_3)_2$) (1-3% on Pt basis) was mixed with 5 g of prepared hydrotalcite support stirred at room temperature for 1 h. The mixture was later dried at 60-80° C. at a duration of 2 to 4 h. The resulted solid was dried in an air oven at 110° C. for 12 h and calcined at 550° C. for 6 h.

The obtained catalyst was denoted as Pt-HT the catalyst. In the present case, the three different types of catalyst named 1% Pt-HT, 2% Pt-HT and 3% Pt-HT contains 1% (0.1 g), 2% (0.2 g), and 3% (0.3 g) of tetra mine platinum nitrate nano hydrate Hydrogenation reactions were conducted in batch mode, in a 160 ml stainless steel autoclave (parr reactor) at various temperatures. leuvlicnic acid (5%), catalyst 0.2 g (reduced in $H_2$ at 480° C.) and water (20 ml) were placed inside the reactor, after which the reactor was closed. Then the system was purged with hydrogen 4 times to remove the air. The whole system was pressurized to 30 bar hydrogen pressure and carried hydrogenation reaction at room temperature (25° C.) for 24 h. At the end of the reaction, the pressure was released very slowly. The catalyst particles were separated by filtration and the product was analyzed by an Agilent 7890 gas chromatograph equipped with a FID (using restek MXT WAX capillary Column 30 m×0.25ID) using reference samples.

This example describes the effect of Pt loading on hydrotalcite catalyst. The results are given in Table 1.

TABLE 1

| Entry | Catalyst code | Catslyst Wt (g) | Conversion (%) | Selectivity/ γ valerolactone |
|---|---|---|---|---|
| 1 | 1 wt % Pt-HT | 0.2 | 78 | >99% |
| 2 | 2 wt % Pt-HT | 0.2 | 90 | >99% |
| 3 | 3 wt % Pt-HT | 0.2 | 100 | >99% |

Example: 3

The hydroltalcite support was prepared by co-precipitation method. The procedure as follows: Salt solution A (100 ml) containing mixture of 0.080 mole $Al(NO_3)_3 \cdot 9H_2O$ and 0.020 mole $Mg(NO_3)_2 6H_2O$ was added drop wise to a basic solution of B (100 ml) containing 0.05 mole $Na_2CO_3$ and 0.17 mole NaOH. The pH was maintained between 9-13 and the mixture was aged for 1 h at room temperature with continuous stirring. Later temperature was raised to 80° C. and continued for 16 to 18 h. The resulted solid was washed with deionised water and dried at 110° C. in an oven for 12 h.

The Pt was deposited by wetness impregnation method. In a typical procedure, a 20 ml solution of 0.2 g of tetramine platinum nitrate nano hydrate ($Pt(NH_3)_4(NO_3)_2$) (2% on Pt basis) was mixed with 5 g of prepared hydrotalcite support stirred at room temperature for 1 h. The mixture was later dried at 60-80° C. at a duration of 2 to 4 h. The resulted solid was dried in an air oven at 110° C. for 12 h and calcined at 550° C. for 6 h.

Hydrogenation reactions were conducted in batch mode, in a 160 ml stainless steel autoclave (parr reactor) at various temperatures. Leuvlicnic acid (5-20%), catalyst 0.2 g (reduced in $H_2$ at 480° C.) and water (20 ml) were placed inside the reactor, after which the reactor was closed. Then the system was purged with hydrogen 4 times to remove the air. The whole system was pressurized to 50 bar hydrogen pressure and carried hydrogenation reaction at room temperature (25° C.) for 24 h. At the end of the reaction, the pressure was released very slowly. The catalyst particles were separated by filtration and the product was analyzed by an Agilent 7890 gas chromatograph equipped with a FID (using restek MXT WAX capillary Column 30 m×0.25ID) using reference samples.

This example describes the effect of leuvlinic acid concentration for its conversion. The analysis results are presented in Table 2

TABLE 2

| Catalyst code | LA (wt %) | Reaction Time (h) | Conversion | Selectivity/γ valerolactone |
|---|---|---|---|---|
| 2 wt % Pt-HT | 5 | 24 | 81 | >99% |
| 2 wt % Pt-HT | 10 | 24 | 60 | >99% |
| 2 wt % Pt-HT | 20 | 24 | 15 | >99% |

Example: 4

The hydroltalcite support was prepared by co-precipitation method. The procedure as follow: Salt solution A (100 ml) containing mixture of 0.080 mole $Al(NO_3)_3 \cdot 9H_2O$ and 0.020 mole $Mg(NO_3)_2 6H_2O$ was added drop wise to a basic solution of B (100 ml) containing 0.05 mole $Na_2CO_3$ and 0.17 mole NaOH. The pH was maintained between 9-13 and the mixture was aged for 1 h at room temperature with continuous stirring. Later temperature was raised to 80° C. and continued for 16 to 18 h. The resulted solid was washed with deionised water and dried at 110° C. in an oven for 12 h.

The Pt was deposited by wetness impregnation method. In a typical procedure, a 20 ml solution of 0.2 g of tetramine platinum nitrate nano hydrate ($Pt(NH_3)_4(NO_3)_2$) (2% on Pt basis) was mixed with 5 g of prepared hydrotalcite support stirred at room temperature for 1 h. The mixture was later dried at 60-80° C. at a duration of 2 to 4 h. The resulted solid was dried in an air oven at 110° C. for 12 h and calcined at 550° C. for 6 h.

Hydrogenation reactions were conducted in batch mode, in a 160 ml stainless steel autoclave (parr reactor) at various temperatures. Leuvlicnic acid (5%), catalyst 0.2 g (reduced in $H_2$ at 480° C.) and water (20 ml) were placed inside the reactor, after which the reactor was closed. Then the system was purged with hydrogen 4 times to remove the air. The whole system was pressurized to 50 bar hydrogen pressure and carried hydrogenation reaction at room temperature (25°

C.) for 2-100 h. At the end of the reaction, the pressure was released very slowly. The catalyst particles were separated by filtration and the product was analyzed by an Agilent 7890 gas chromatograph equipped with a FID (using restek MXT WAX capillary Column 30 m×0.25ID) using reference samples.

This example describes the effect of reaction time on conversion of leuvliic acid conversion. The analysis results are presented in Table 3

TABLE 3

| Entry | Catalyst code | Reaction Time (h) | Conversion (%) | Selectivity/γ valerolactone |
|---|---|---|---|---|
| 1 | 2 wt % Pt-HT | 2 | 34 | >99% |
| 2 | 2 wt % Pt-HT | 5 | 45 | >99% |
| 3 | 2 wt % Pt-HT | 8 | 57 | >99% |
| 4 | 2 wt % Pt-HT | 12 | 66 | >99% |
| 5 | 2 wt % Pt-HT | 22 | 75 | >99% |
| 6 | 2 wt % Pt-HT | 24 | 81 | >99% |
| 7 | 2 wt % Pt-HT | 30 | 83 | >99% |
| 8 | 2 wt % Pt-HT | 35 | 85 | >99% |
| 9 | 2 wt % Pt-HT | 47 | 86 | >99% |
| 10 | 2 wt % Pt-HT | 60 | 89 | >99% |
| 11 | 2 wt % Pt-HT | 75 | 90 | >99% |
| 12 | 2 wt % Pt-HT | 100 | 90 | >99% |

Example: 5

The hydroltalcite support was prepared by co-precipitation method. The procedure as follows: Salt solution A (100 ml) containing mixture of 0.080 mole $Al(NO_3)_3.9H_2O$ and 0.020 mole $Mg(NO_3)_26H_2O$ was added drop wise to a basic solution of B (100 ml) containing 0.05 mole $Na_2CO_3$ and 0.17 mole NaOH. The pH was maintained between 9-13 and the mixture was aged for 1 h at room temperature with continuous stirring. Later temperature was raised to 80° C. and continued for 16 to 18 h. The resulted solid was washed with deionised water and dried at 110° C. in an oven for 12 h.

The Pt was deposited by wetness impregnation method. In a typical procedure, a 20 ml solution of 0.2 g of tetramine platinum nitrate nano hydrate $(Pt(NH_3)_4(NO_3)_2)$ (2% on Pt basis) was mixed with 5 g of prepared hydrotalcite support stirred at room temperature for 1 h. The mixture was later dried at 60-80° C. at a duration of 2 to 4 h. The resulted solid was dried in an air oven at 110° C. for 12 h and calcined at 550° C. for 6 h.

Hydrogenation reactions were conducted in batch mode, in a 160 ml stainless steel autoclave (parr reactor) at various temperatures. leuvlicnic acid (5%), catalyst 0.2 g (reduced in $H_2$ at 480° C.) and water (20 ml) were placed inside the reactor, after which the reactor was closed. Then the system was purged with hydrogen 4 times to remove the air. The whole system was pressurized to 20-50 bar hydrogen pressure and carried hydrogenation reaction at room temperature (25° C.) for 24 h. At the end of the reaction, the pressure was released very slowly. The catalyst particles were separated by filtration and the product was analyzed by an Agilent 7890 gas chromatograph equipped with a FID (using restek MXT WAX capillary Column 30 m×0.25ID) using reference samples.

This example describes the effect of $H_2$ pressure on conversion of leuvlicnic acid. The analysis results are presented in Table 4

TABLE 4

| Entry | Sample code | Hydrogen pressure (bar) | Conversion (%) | Selectivity/ γ valerolactone |
|---|---|---|---|---|
| 1 | 2 wt % Pt-HT | 20 | 65 | >99% |
| 2 | 2 wt % Pt-HT | 30 | 72 | >99% |
| 3 | 2 wt % Pt-HT | 40 | 74 | >99% |
| 4 | 2 wt % Pt-HT | 50 | 81 | >99% |

Example: 6

The hydroltalcite support was prepared by co-precipitation method. Salt solution A (100 ml) containing mixture of 0.080 mole $Al(NO_3)_3.9H_2O$ and 0.020 mole $Mg(NO_3)_26H_2O$ was added drop wise to a basic solution of B (100 ml) containing 0.05 mole $Na_2CO_3$ and 0.17 mole NaOH. The pH was maintained between 9-13 and the mixture was aged for 1 h at room temperature with continuous stirring. Later temperature was raised to 80° C. and continued for 16 to 18 h. The resulted solid was washed with deionised water and dried at 110° C. in an oven for 12 h.

The Pt was deposited by wetness impregnation method. In a typical procedure a 20 ml solution of 0.2 g of tetramine platinum nitrate nano hydrate $(Pt(NH_3)_4(NO_3)_2)$ (3% on Pt basis) was mixed with 5 g of prepared hydrotalcite support stirred at room temperature for 1 h. The mixture was later dried at 60-80° C. at a duration of 2 to 4 h. The resulted solid was dried in an air oven at 110° C. for 12 h and calcined at 550° C. for 6 h.

Hydrogenation reactions were conducted in batch mode, in a 160 ml stainless steel autoclave (parr reactor) at various temperatures. leuvlicnic acid (5%), catalyst 0.2 g (reduced in $H_2$ at 480° C.) and water (20 ml) were placed inside the reactor, after which the reactor was closed. Then the system was purged with hydrogen 4 times to remove the air. The whole system was pressurized to 50 bar hydrogen pressure and carried hydrogenation reaction between 25 to 75° C. for 5 h. At the end of the reaction, the pressure was released very slowly. The catalyst particles were separated by filtration and the product was analyzed by an Agilent 7890 gas chromatograph equipped with a FID (using restek MXT WAX capillary Column 30 m×0.25ID) using reference samples.

This example describes the effect of reaction temperature on conversion of Leuvlinic acid. The analysis results are presented in Table 5

TABLE 5

| Entry | Catalyst code | Reaction temperature (° C.) | Conversion (%) | Selectivity/ γ valerolactone |
|---|---|---|---|---|
| 1 | 2 wt % Pt-HT | 25 | 45 | >99% |
| 2 | 2 wt % Pt-HT | 40 | 62 | >99% |
| 3 | 2 wt % Pt-HT | 50 | 79 | >99% |
| 4 | 2 wt % Pt-HT | 75 | 100 | >99% |

Advantages of the Invention

The main advantages of the present invention are:
1. The process of the present invention converts levulinic acid to γ-valerolactone in a single step with a single catalyst.
2. The process of the present invention hydrogenation of levulinic acid at room temperature.

3. The process shows conversion of levulinic acid up to 900/%.
4. The process provides selectivity of γ-valerolactone up to >99%.
5. The process provides good conversion even at low hydrogen pressure.
6. The catalyst is used in very low amounts.
7. The process does not produce any major by-products which is also a major advantage of the process.

We claim:

1. A process for the production of γ-valerolactone comprising the steps:
    a) precipitating a hydrotalcite support from an aqueous solution of nitrate salts of aluminum and magnesium that are present in a molar ratio of 80:20;
    b) impregnating the hydrotalcite support with a solution of $Pt(NH_3)_4(NO_3)_2$ (1-3%) to yield a Pt loaded hydrotalcite;
    c) calcining the Pt loaded hydrotalcite as obtained from step (b) at 260-550° C. in air;
    d) reducing the Pt loaded hydrotalcite as obtained from step (c) in hydrogen gas at 260-480° C. to obtain a platinum supported hydrotalcite;
    e) hydrogenating levulinic acid in water in the presence of the platinum supported hydrotalcite catalyst as obtained in step (d) in a high pressure stirrer reactor at 25° C. to 100° C. and 20-50 bar hydrogen gas while stirring for a period of 2-100 h to obtain γ-valerolactone.

2. A process according to claim 1, wherein hydrogenating levulinic acid (LA) is carried out at a temperature in the range between 75–100° C.

3. A process according to claim 1, wherein hydrogenating levulinic acid (LA) is carried out for a time in the range 75-100 h.

4. A process according to claim 1, wherein hydrogenating levulinic acid (LA) is carried out at a pressure in the range of 40-50 bar hydrogen pressure.

5. A process according to claim 1, wherein the levulinic acid concentration in step (e) is in the range of 5-20%.

* * * * *